United States Patent [19]

Pappas et al.

[11] Patent Number: 4,955,919

[45] Date of Patent: Sep. 11, 1990

[54] MULTI-COMPONENT JOINT PROSTHESIS WITH INCREASED WALL FLEXIBILITY FACILITATING COMPONENT ASSEMBLY

[76] Inventors: Michael J. Pappas, 61 Gould Pl., Caldwell, N.J. 07006; Frederick F. Buechel, 76 Crest Dr., South Orange, N.J. 07079

[21] Appl. No.: 712,370

[22] Filed: Mar. 15, 1985

Related U.S. Application Data

[63] Continuation-in-part of Ser. No. 492,133, May 6, 1983, abandoned.

[51] Int. Cl.$^5$ ............................................... A61F 2/32
[52] U.S. Cl. ..................................................... 623/22
[58] Field of Search ...................... 623/16, 18, 19, 22, 623/23

[56] References Cited

U.S. PATENT DOCUMENTS

| | | | |
|---|---|---|---|
| D. 249,957 | 10/1978 | Eicher et al. | 623/22 |
| 3,584,318 | 6/1971 | Scales et al. | 623/22 |
| 4,365,358 | 12/1982 | Judet et al. | 623/22 |
| 4,624,674 | 11/1986 | Pappas et al. | 623/22 |

Primary Examiner—David J. Isabella
Attorney, Agent, or Firm—Anthony J. Casella; Gerald E. Hespos

[57] ABSTRACT

Multi-component joint prosthesis including first and second components for being assembled together and the assembly of which requires the application of assembly forces, e.g. a hip joint prosthesis including an acetabular cup and plastic bearing liner for being assembled together and wherein such assembly requires the application of assembly forces. One or both of the components being a segmented open shell including a wall having a major load supporting segment resisting the assembly force removed which increases the flexibility of the wall and facilitates assembly of the components, e.g. in one hip prosthesis embodiment an inferior segment of the wall of each component is removed to increase the flexibility of the wall and facilitate the assembly of the acetabular cup and plastic bearing liner.

25 Claims, 10 Drawing Sheets

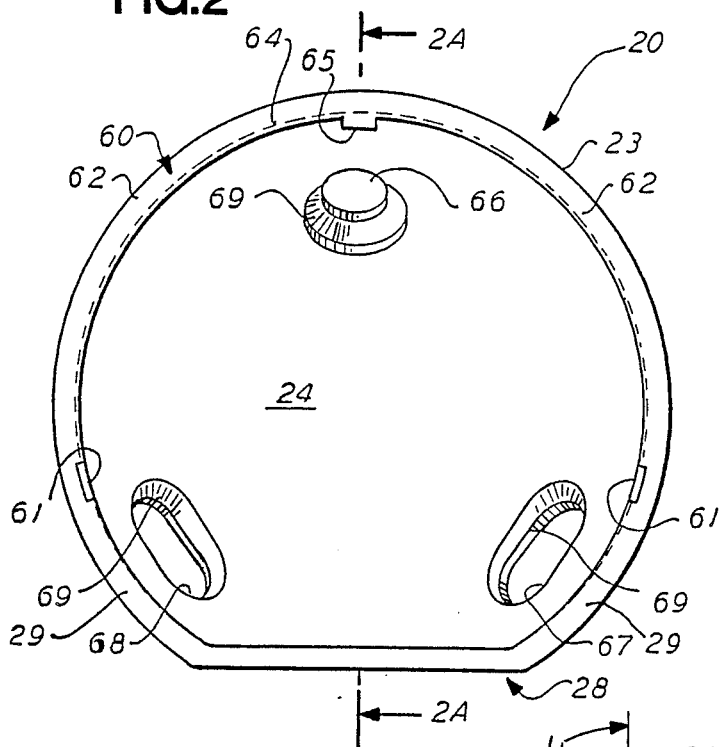
FIG.2
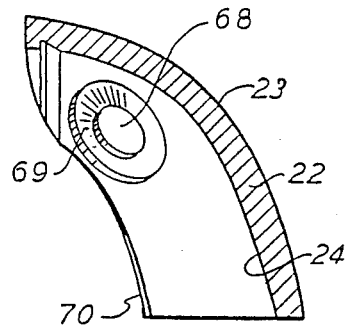
FIG.2B
FIG.2A
FIG.2C
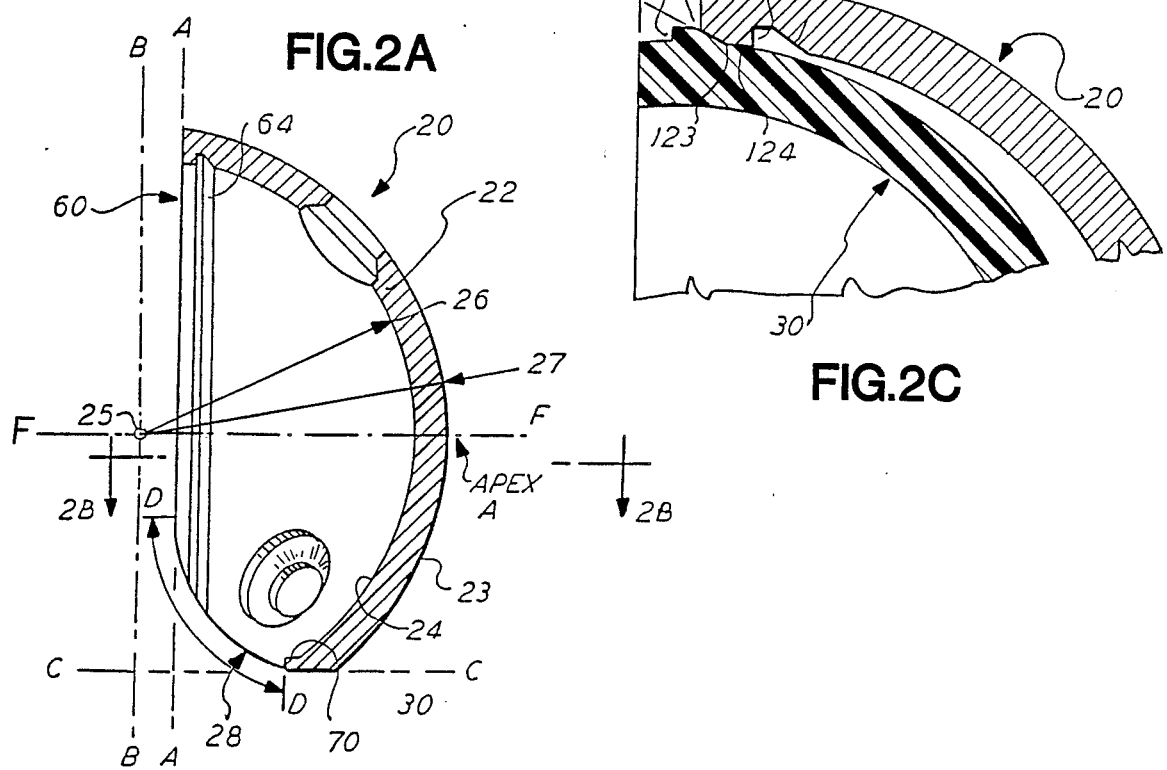

FIG.4
FIG.4A
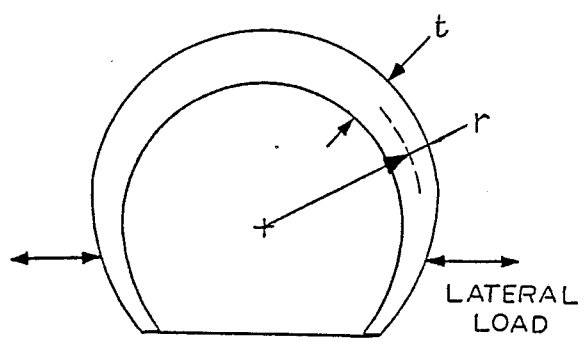
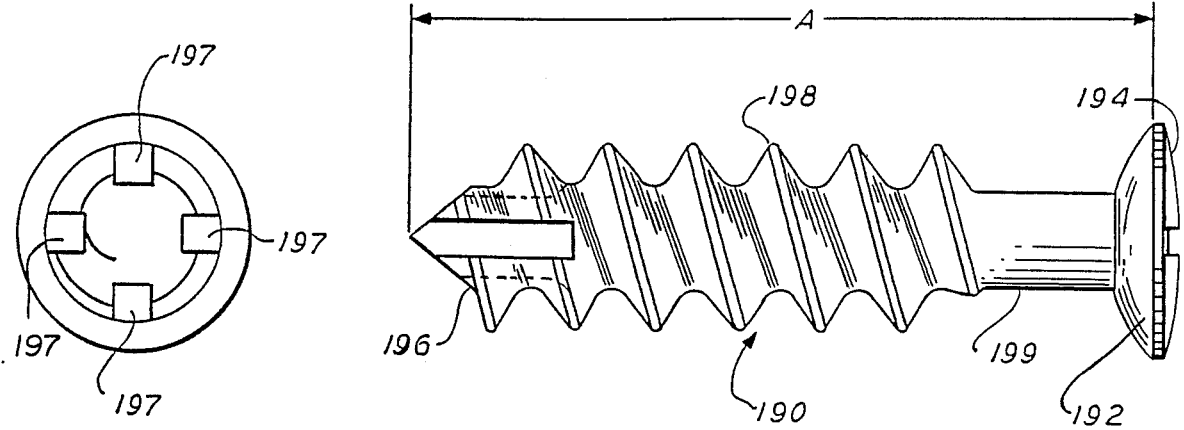
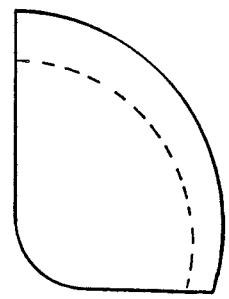
FIG.7B
LATERAL VIEW
FIG.7A
ANTERIOR VIEW
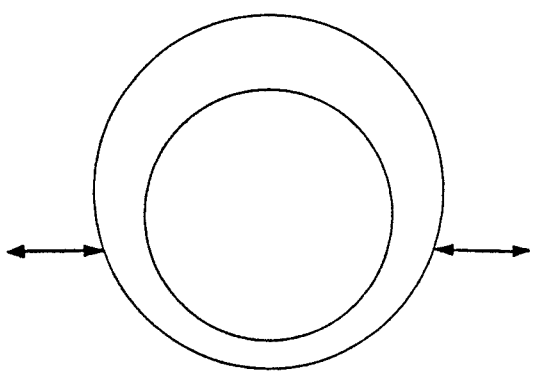
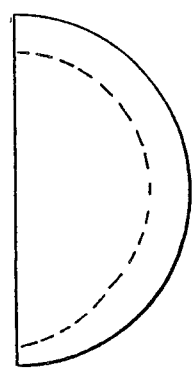
FIG.7D
LATERAL VIEW
FIG.7C
ANTERIOR VIEW

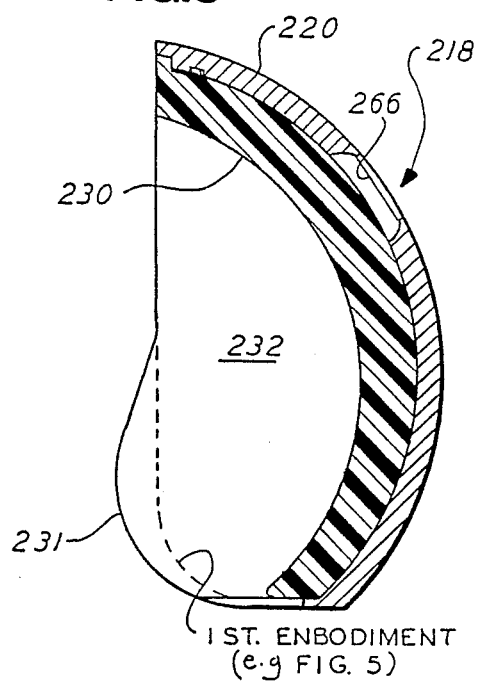
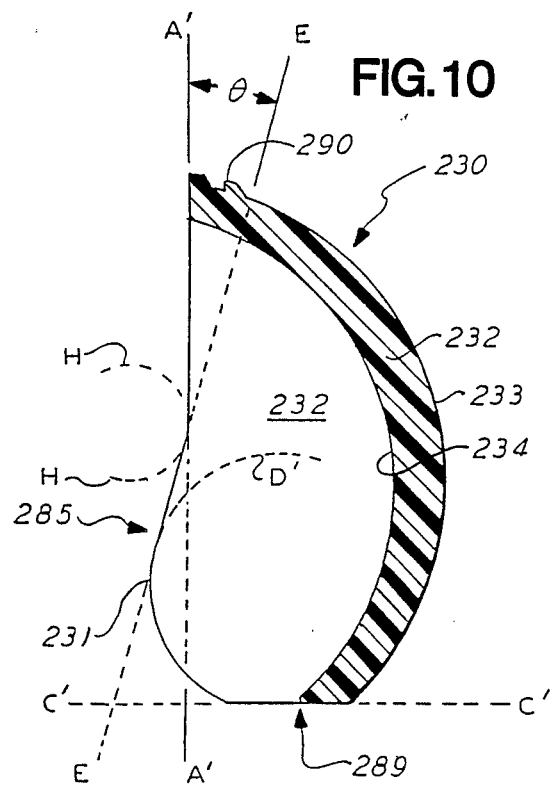
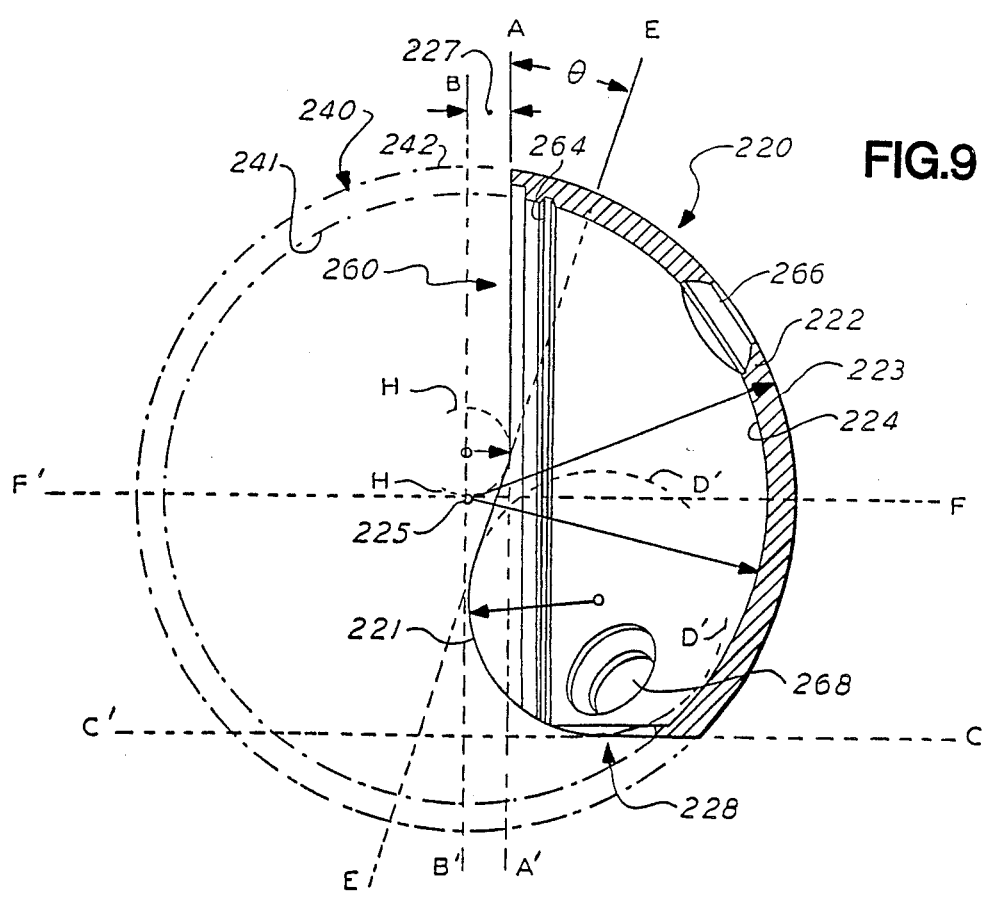

MULTI-COMPONENT JOINT PROSTHESIS WITH INCREASED WALL FLEXIBILITY FACILITATING COMPONENT ASSEMBLY

CROSS REFERENCE TO RELATED APPLICATION

This application is a continuation-in-part of U.S. patent application Ser. No. 492,133 filed May 6, 1983, now abandoned and entitled MULTI-COMPONENT PROSTHESIS WITH INCREASED WALL FLEXIBILITY FACILITATING COMPONENT ASSEMBLY, Michael J. Pappas and Frederick F. Buechel, inventors.

BACKGROUND OF THE INVENTION

This invention relates generally to a new and improved joint prosthesis, and more particularly relates to an improved multi-component hip joint prosthesis, such as for example a multi-component hip joint prosthesis, wherein at least one of the components is a segmented open shell to provide a wall of increased flexibility to facilitate assembly of the prosthesis components.

The conventional prior art total hip prosthesis typically includes a metal femoral head fixtured to the femur and a plastic, generally ultra-high molecular weight (UHMWPe), cup fixtured by cement to the acetabulum such as the type disclosed in U.S. Pat. No. 4,123,806 issued Nov. 7, 1978 to Amstutz et al. The prior art also discloses the use of hip prostheses including metal backed acetabular components in which the acetabular component consists of a metal cup with a plastic bearing insert; examples of such prostheses are given in U.S. Pat. No. 3,840,904 issued Oct. 15, 1979 to Tronzo and U.S. Pat. No. 3,903,549 issued Sept. 9, 1975 to Deyerle. Metal backed acetabular hip prosthesis components have several advantages. The metal or rigid outer acetabular cup produces a much more uniform stress distribution at the interface between the cup and the acetabulum with lower peak forces or stress thereby improving the possibility of long term fixation. Rigidity of the metal outer acetabular cup also reduces distortion of the plastic liner improving its sphericity and therefore contact with the metal femoral head of the hip prosthesis thereby improving conditions for wear resistance. Further, the use of a separate bearing insert allows replacement of the insert if the insert is damaged intraoperatively or if the insert becomes excessively worn as a result of long term use or if as a result of some problem revision is necessary which involves a change in the insert bearing. For example, in the event of revision from a surface replacement type hip prosthesis which has a fairly large diameter head to a stem type femoral prosthesis which includes usually a smaller diameter head one may simply remove the bearing liner leaving the metal acetabular cup affixed to bone and replace the liner with another liner or insert of appropriate size for the revised unit. Such revision can, therefore, be made without disturbing the acetabular fixation thereby preventing damage to the acetabular bone.

There is, however, a potential disadvantage associated with the use of a rigid or metal acetabular cup. In the event that a load is applied near the rim of the acetabular cup, the elastic properties of the underlying bone combined with the rigidity of the cap can produce a situation in which the opposite rim tends to be lifted off of its bony bed. This tends to produce tensile loads on the cup and such tensile loads are undesirable in maintaining long term fixation.

In the prosthesis disclosed in the Tronzo patent, an interlock 26 and interlocking groove 28 as described in FIGS. 2-8 of Tronzo are used to prevent rotation of the liner relative to the cup. This connection, however, is not resistant to a tensile withdrawal of the cup from the liner. Such withdrawal can occur as a result of traction forces due to a layer of liquid interposed between the femoral component and the plastic liner coupled with distraction of the femur from the acetabulum during normal activity. Such a situation can, therefore, produce withdrawal of the plastic bearing from the acetabular cup producing dislocation of the prosthetic component.

The prosthesis described in the Deyerle patent uses an arcuate ridge 32 which engages an arcuate slot 44 as shown in FIGS. 1, 5 and 6 of Deyerle to restrict relative rotation. The Deyerle device uses screws by making use of an annular liner (not identified by number) in conjunction with a retaining screw 30 in order to trap the liner in the cup. This design, however, experiences difficulty in liner removal because removal of the liner requires removal of the screws from the bone which may produce damage to the bone. Further, the use of such a connection resistant against tensile loading requires the use of screws and many surgeons would prefer in some applications not to use screws for fixation.

Both the Tronzo and Deyerle prostheses use screws. Neither, however, provides the ability of the screws to change their angular orientation significantly to facilitate fixation. Further, neither provides screws near the inferior rim to minimize the possible lifting of the inferior rim as a result of loads applied near the superior rim. Such loads are normal in walking and may exceed eight times body weight in stair climbing and descent. Since the angular orientation of the screw is not adjustable in Tronzo and Deyerle devices, these screw configurations cannot take maximum advantage of possible superior bone stock for screw implantation. Further, Deyerle and Tronzo prostheses both make use of either screws or spikes for fixation. However, when such acetabular components are used with cement, such spikes or screws may not be necessary for fixation and their use makes the operative procedure more difficult and introduces additional damage to the bone.

U.S. Pat. No. 3,608,096 to Link discloses a prosthesis which uses a relieved face on the acetabular shell where a segment of the shell is removed by means of an oblique cut (not identified by number) as described in Column 2, lines 69-72 and Column 3, lines 1-3 to provide a better approximation to the shape of the natural acetabulum so as to increase clearance reducing possible impingement with the femur during certain kinds of activity as described in Column 3, lines 26-29. Further, the outside section 3 as shown in FIG. 1 of the Link patent is eccentric to the cavity 2 although the nature and reason for this eccentricity are not described by Link. Although this oblique and simple relief provides improvement in fit and clearance, still better fit and clearance can be provided by a somewhat more complex relief of the inferior face of the acetabular component.

SUMMARY OF THE INVENTION

Assembly of the components of a multi-component prosthesis is facilitated by constructing at least one of the components as a non-symmetrical segmented open shell whereby the segmenting of the shell increases the flexibility of the shell wall which flexibility in turn facilitates component assembly; such flexibility also enhances the engagement of retaining means for retaining the components together upon assembly.

Screws utilized to secure a prosthesis component to a bone are recessed within the seat of a screw hole formed in the component for receiving the screw and generally area contact is achieved between the underside of the screw head and the seat of the screw hole by making both the underside of the screw head and the screw hole seat spherical-additionally, a second component engaging the first component may be provided with a recess overlying the screw hole whereby in the event the screw head extends upwardly out of the screw seat the recess accommodates the screw head.

As used in the context of the present invention, and as used in the specification and appended claims, the term "open shell" means a shell segment produced by the cutting of a closed shell (i.e. a shell without openings) by means of a single cutting plane or planar cutting surface cutting through both the exterior and interior surfaces of the shell; the term "segmented open shell" means a shell segment produced by cutting an open shell by additional cutting surfaces or by cutting a closed shell by a non-planar cutting surface, e.g. a cylindrical cutting surface by more than one cutting plane or planar cutting surface. The generation of slots is not considered segmentation in the context of the present invention since the generation of a slot is the equivalent of splitting the shell rather than removal of a shell segment; although slotting normally involves removal of a thin segment, such removal is incidental to function.

DESCRIPTION OF THE DRAWINGS

FIG. 2 is a front elevational view of a metal acetabular cup of the present invention, FIG. 2A is a cross-sectional view taken in FIG. 2 along the line 2A—2A and in the direction of the arrows, FIG. 2B is a cross-sectional view taken along the line 2B—2B in FIG. 2A and in the direction of the arrows, and FIG. 2C is a partial cross-sectional view illustrating the manner of assembly of the acetabular cup and bearing liner retaining means of the present invention;

FIG. 4 is a side elevational view of a screw of the present invention and FIG. 4A is a left end view of the screw of FIG. 4;

FIGS. 7A-7D are diagrammatical illustrations of a teaching of the present invention as to the increase in flexibility of the wall of a shell to facilitate assembly of prosthesis components;

FIGS. 8-10 are cross-sectional views of a further alternate embodiment of an acetabular cup and plastic bearing liner of the present invention;

DESCRIPTION OF THE PREFERRED EMBODIMENT

Figure 1:
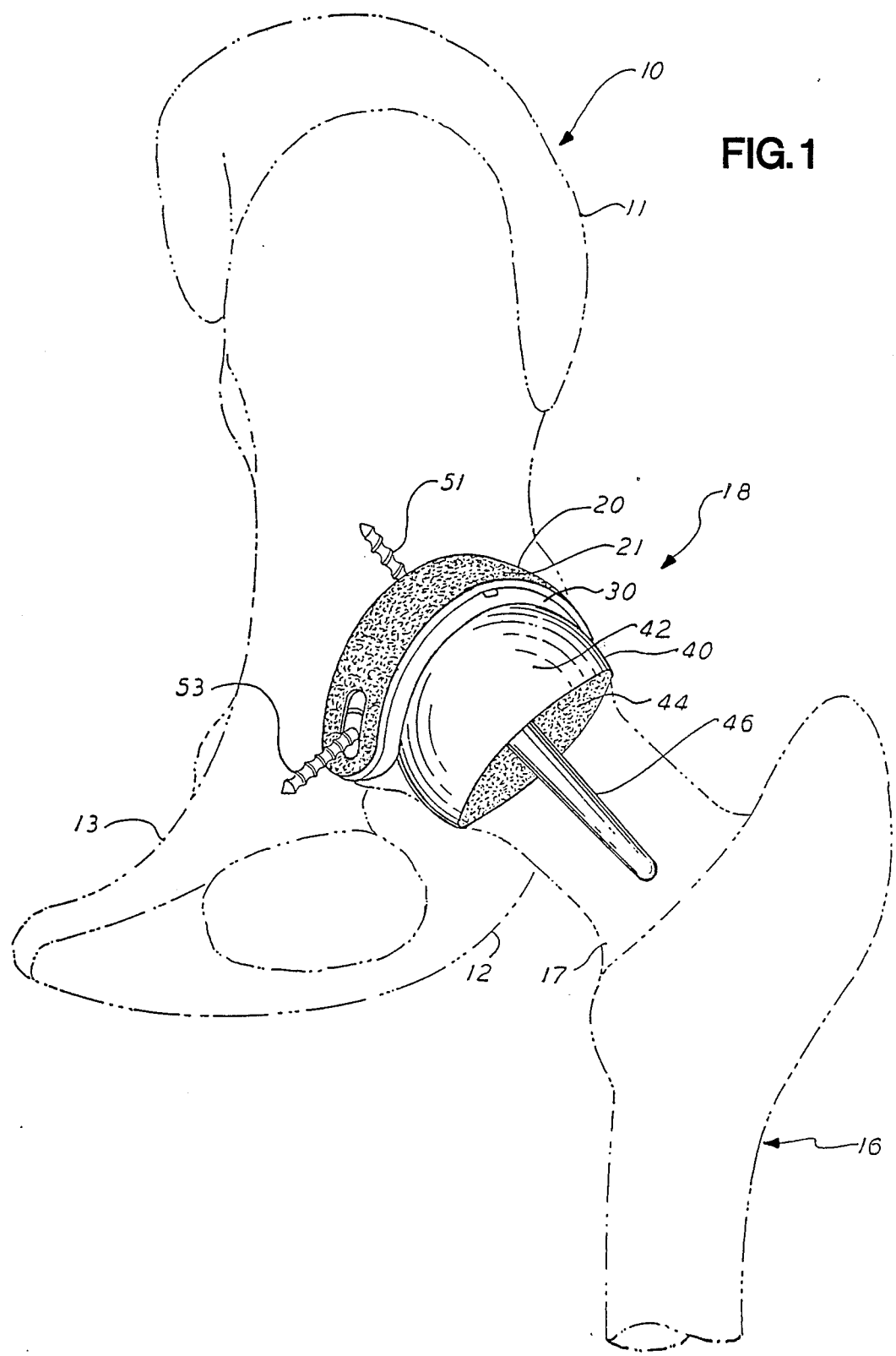
FIG. 1 is a diagrammatical illustration of a surface replacement hip joint prosthesis embodying the present invention and shown diagrammatically as being fixtured by bone ingrowth to the hip bone and femur.

Referring now to FIG. 1, there is shown a diagrammatical illustration of a natural innominate or hip bone 10 including the ilium 11, the ischium 12 and the pubis 13 and a natural femur 16 having a neck 17. Also shown diagrammatically is a hip joint prosthesis embodying the present invention and indicated by general numerical designation 18; the hip joint prosthesis 18 as shown is of the type commonly referred to in the art as a surface replacement hip joint prosthesis but it will be understood that the present invention is not limited to the surface replacement type prosthesis but has wide application to other types of prostheses such as other types of hip and shoulder prostheses; the prosthesis 18 is shown diagrammatically as being implanted in or fixtured to the hip or pelvic bone 10, or more particularly to the portion of the hip bone providing the acetabulum, or acetabular socket and to the femur 16. The hip joint prosthesis 18 includes a metal acetabular cup 20, a plastic bearing liner or plastic acetabular cup 30 and a metal femoral component or cap 40 of the surface replacement type but may be used with other femoral prostheses such as those commonly referred to as the femoral stem type prostheses.

Figure 6:
FIG. 6 is a diagrammatical illustration illustrating the assembly of the femoral cap to the resected head of a natural femur.

In the embodiment shown, the metal acetabular cup 20 is provided with a porous outer surface or coating 21 into which the hip bone may grow for permanent fixation. The cup 20 is temporarily fixtured to the hip bone 10 by the use of metal screws 51, 52 (not shown) and 53 which screws are used primarily to establish temporary fixation of the acetabular cup 20 to the hip bone 10 during the period of time that is required for biological bone or bony ingrowth to occur into the porous coating 21 to provide permanent fixation or to provide augmentation to fixation by use of bone cement. In the preferred embodiment, the metal acetabular cup 20 is temporarily fixtured to the hip bone by the three metal screws, metal screw 51 being screwed into the ilium 11, metal screw 52 (not shown) being screwed into the ischium 12, and metal screw 53 being screwed into the pubis 13. The plastic bearing liner or cup 30 is snapped into the metal acetabular cup 20, in a manner described in detail below, and its inner surface provides the acetabular articulation surface. The metal femoral cap 40 is provided with a highly polished exterior surface 42 providing the femoral articulation surface, a generally hollow interior having an interior porous surface indicated by general numerical designation 44 into which femur bone may grow to permanently fixture the femoral cap 40 to the resected head 19 of the femur 16 as shown in FIG. 6 or which porous surface is used to improve cement fixation, and a relatively smooth or polished metal stem 46 which is used primarily for alignment purposes and to provide some resistance against fracture of the femoral neck but the relatively smooth surface of the metal stem 46 is not a fixation surface. Temporary fixation, during the time required for permanent bone ingrowth fixation to occur, is provided by a press fit between the interior surface 44 and the resected femur head 19 and a press fit between the stem 46 and a hole 47 (FIG. 6) drilled centrally in the resected femur head 19 and femur neck 18. The femoral cap 40 shown in FIG. 1 is the subject of a copending application by the same inventors as the present invention.

Referring now to FIGS. 2, 2A, and 2B, it will be noted that the acetabular cup 20 is an asymmetrical, substantially hemispherical cup having a wall 22, a relatively thin wall, defined by concentric outer and inner surfaces 23 and 24, respectively, having a common center 25 (FIG. 2A) from which spherical radii 26 and 27 are struck. The acetabular cup, at its inferior portion indicated by general numerical designation 28, is relieved as may be best seen in FIG. 2A.

One embodiment of the acetabular cup is shown in FIGS. 2-2B. Cup 20 is a multiply segmented shell of revolution, i.e. a segmented open shell, having a generating axis F—F and being of uniform wall thickness and having concentric inner and outer surfaces. The face 60 of the cup is a surface produced by the intersection of a first cutting plane A—A perpendicular to a plane of symmetry (such plane of symmetry lying in the plane of the drawing) of the cup where the first cutting plane or planar cutting surface A—A partially defining the face 60 of the cup is closer to a parallel plane B—B through the center of the sphere defining the outer and inner surfaces 23 and 24, respectively, of the cup. The cup is segmented by an inferior surface defined by the intersection of a second cutting plane or planar cutting surface C—C perpendicular to the plane of symmetry and to the first cutting plane B—B defining the face 60 of the cup. The cup has a transition surface 29 (FIG. 2) defined by an intersection of the shell of revolution with a segment D—D of a cylindrical cutting surface perpendicular to the plane of symmetry and tangent to the first and second cutting surfaces or planes defining the face and inferior surfaces, respectively. Segmentation of the acetabular cup 20 by cutting planes or surfaces A—A, B—B and C—C causes the cup to be a "segmented open shell" as defined above.

A ridge 70 (lower portion of FIG. 2A) protrudes from the inferior aspect of the cup adjacent to the inner surface 24. An annular groove 64 cut into the inside surface is employed where this groove lies in a plane parallel to the first cutting plane and adjacent to it. The cup may be provided at its superior portion, FIG. 2, with a radially inwardly directed key 65 extending inwardly a distance from the face of the cup. Additionally, the cup 20 may be provided with a pair of generally opposed slots 61—61 extending inwardly from the face 60 of the cup, the slots 61—61 being provided, generally, as may be noted in FIG. 2, at the lateral or side portions of the cup 20. Further, the cup may be provided with three apertures or screw holes 66, 67 and 68 each for receiving a metal screw, such as for example the metal screw 190 of FIG. 4. The apertures may be provided with a recessed spherical seat 69 for accommodating any misalignment with the spherical underside 92 of the screw head 94 of FIG. 4 with the screw head remaining entirely within the recess. Further, to permit the screw inserted through one of the apertures to engage the best available bone accessible through the aperture, the spherical seats may be made oblong as shown more clearly with regard to apertures 67 and 68 in FIG. 2.

Figure 3:
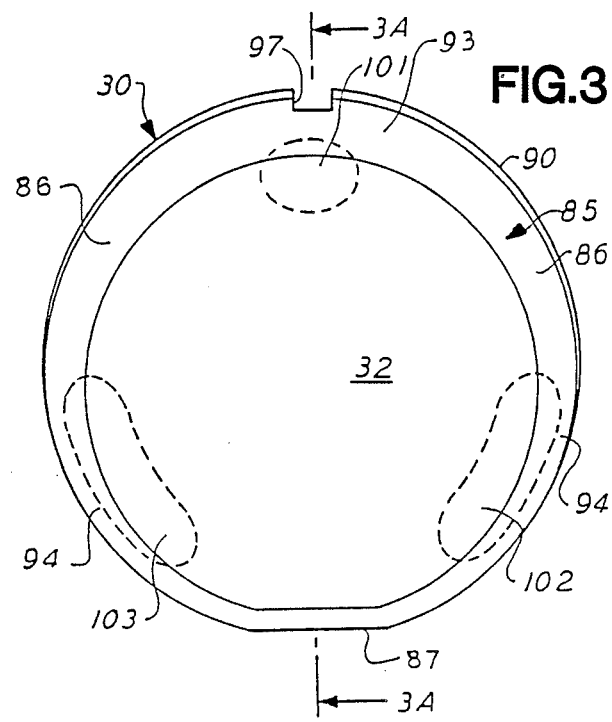
FIG. 3 is a front elevational view of a bearing liner embodying the present invention.
Figure 3B:
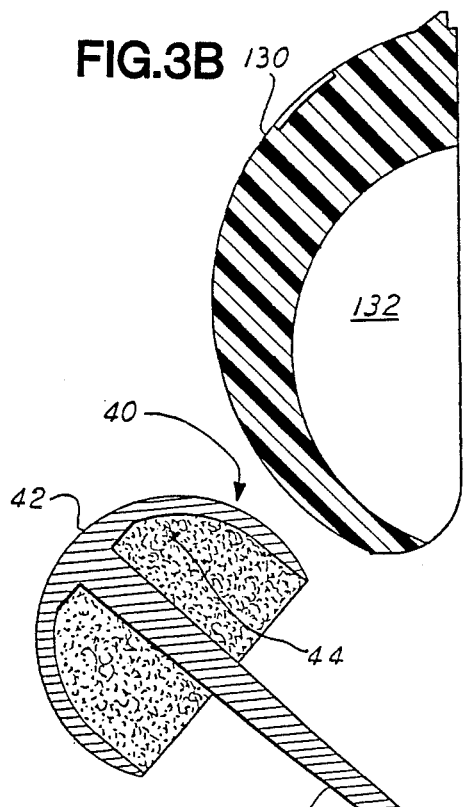
FIG. 3B is a cross-sectional view of an alternate bearing liner embodiment of the present invention, similar to FIG. 3A but taken in a direction opposite to the arrows 3A—3A in FIG. 3.
Figure 3A:
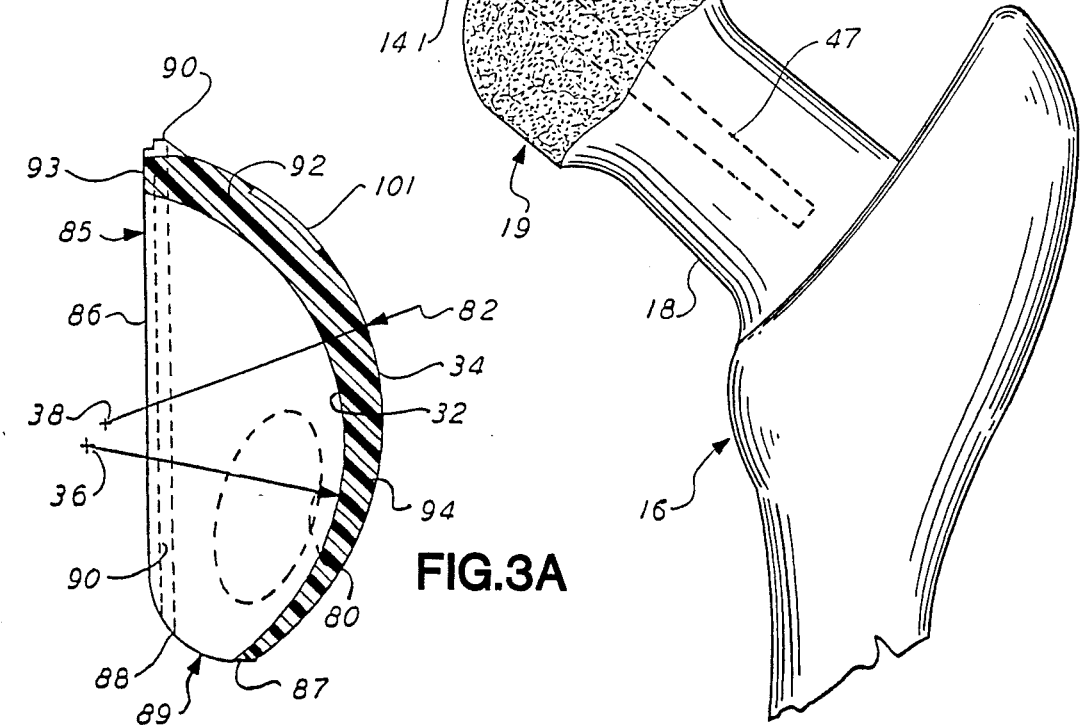
FIG. 3A is a cross-sectional view taken generally along the line 3A—3A in FIG. 3 and in the direction of the arrows.

Referring now to FIGS. 3, 3A and 3B, it will be noted that the plastic bearing liner 30 is an asymmetrical, eccentric, substantially hemispherical cup defined by eccentric inner surface 32 and outer surface 34. It will be noted in FIG. 3A that the inner and outer spherical surfaces 32 and 34 have mutually displaced respective spherical centers 36 and 38 with the spherical radius 80 of the inner surface 32 being struck from the spherical center 36 and with the spherical radius 82 of the outer spherical surface 34 being struck from the spherical center 38. The liner 30 is further provided with a face indicated by general numerical designation 85, complementary in shape to the face 60 of the acetabular cup 20. The liner 30 used in conjunction with the acetabular cup embodiment shown in FIGS. 2-2A is provided with a flat region 86 and a curved or cylindrical region 88 and a flat region 87 causing the liner 30 to be relieved at its inferior portion indicated by general numerical designation 89, in the same manner as the metal acetabular cup 20 of FIG. 2A, i.e. by being segmented by cutting planes such as A—A₁, C—C and D—D₁ of FIG. 2A, such segmentation including such inferior relief causes the liner 30 to be a "segmented open shell" as defined above. The outer surface 34 of the plastic bearing liner 30, as may be best seen in FIG. 3A, is provided with an interrupted annular ridge 90 which annular ridge is interrupted by the relieved inferior portion 89 of the cup or by the circular or cylindrical portion 88 of the face 85. The eccentric inner and outer surfaces 32 and 34, respectively, provide the plastic bearing liner 30 with a wall 92, as may be best seen in FIG. 3A, which wall is thicker at its superior portion 93 and which is thinner at its lateral portions 94—94 (FIG. 3) adjacent the inferior portion 89 of the liner. This is done in order to provide a greater thickness of bearing allowing greater wear in the superior aspect where most wear occurs and to produce a somewhat thinner sidewall laterally anteriorly and posteriorly thereby increasing flexibility of the wall in the region where the wall must be compressed in order to assemble the bearing insert into the acetabular cup. Further, as may be best seen in FIG. 3, the plastic bearing liner 30 may be provided at its superior portion 93 with a radially inwardly extending keyway 97 for receiving the key 65 of the acetabular cup 20, FIG. 2. The outer surface 34 of the plastic bearing liner 30 may be provided with a plurality of mutually displaced recesses 101, 102 and 103 for overlying the apertures 66, 67 and 68 of FIG. 2 and their spherical, and oblong spherical, seats 69 which help prevent contact between the liner and the screw head where the screw is not properly seated. The interrupted annular ridge 90 is complementary to and closely matches the interrupted annular ridge 64 of the acetabular cup 20, the outer surface 34 of the plastic bearing liner 30 closely matches the spherical inner surface 24 of the acetabular cup 20 and the spherical inner surface 32 of the plastic bearing liner 30 provides the acetabular articulation surface.

Figure 5:
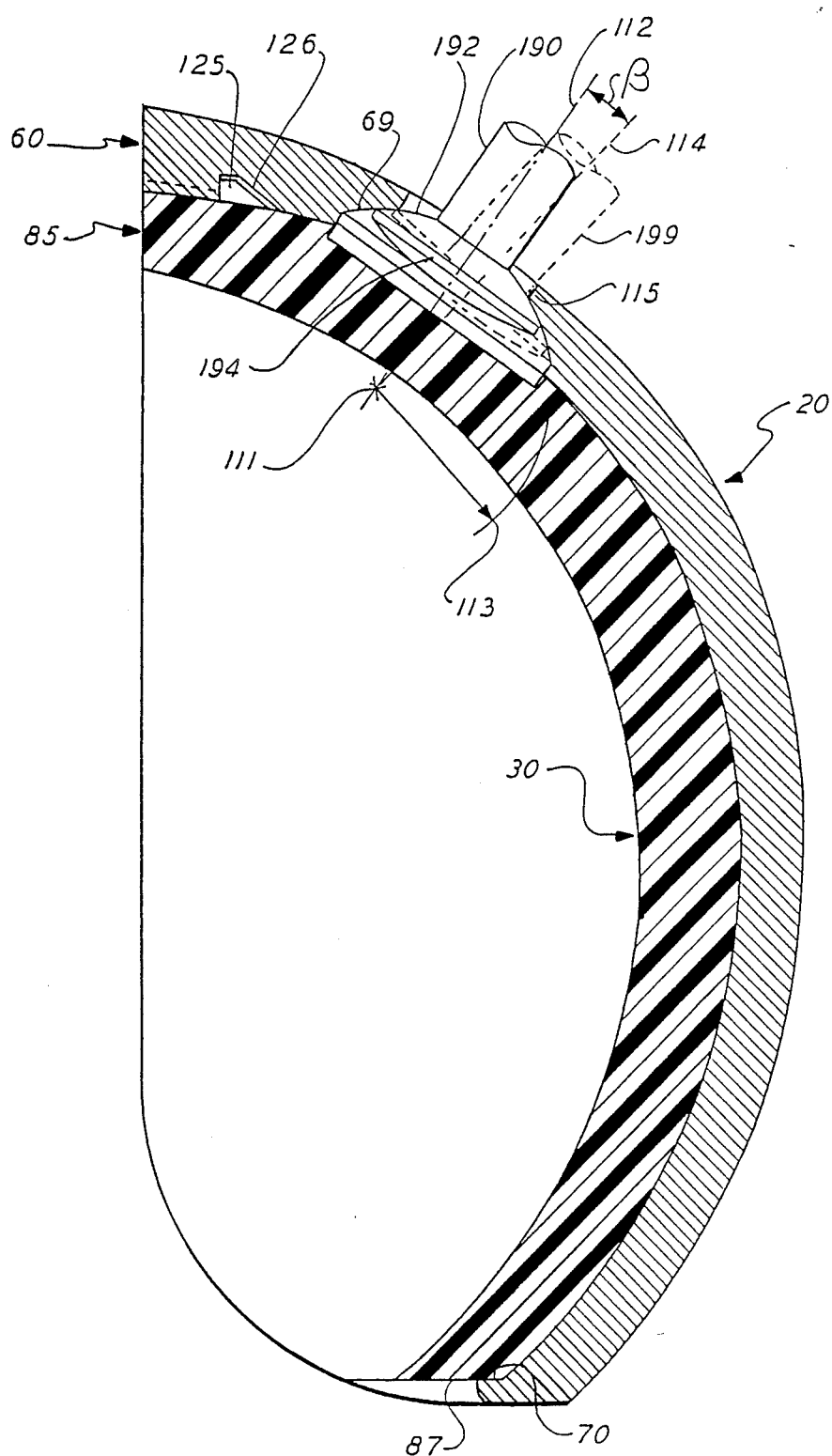
FIG. 5 is an assembly view of the acetabular cup of the present invention and a bearing liner of the present invention, the bearing liner being an alternate embodiment of the liner of FIG. 3, and such illustration showing the assembly as it would look in cross-section were such cross-sectional assembly view to be taken along lines such as 2A—2A in FIG. 2 and 3A—3A in FIG. 3.

The inferior flat surface 87 of insert 30 engages the ridge 70 on the acetabular cup 20 restraining, in conjunction with key 65 and keyway 97, axial rotation of insert 30 with respect to acetabular cup 20 about generating axis F—F as shown in FIG. 5.

A cross-section of the partially assembled insert and acetabular cup in the region of the interconnecting ridge and groove is shown in FIG. 2C. The ridge and groove faces 125 and 126, respectively, are substantially parallel to the faces 85 and 60 of the insert and cup, respectively. The medial aspect of the ridge is at an angle $\mu$ relative to the face. Upon assembly using inward forces with substantial force components parallel to the generating axis (F—F of FIG. 2A), the medial aspect of the ridge 90 engages an edge 123 of the interior surface 24 of the acetabular cup. Such engagement produces forces with substantial lateral components generally perpendicular to the generating axis, such components tending to compress the insert or expand the acetabular cup 20. Since the side walls of the insert or cup due to the segmentation described are relatively laterally flexible sufficient deformation of the insert and cup is easily produced to allow the ridge 90 to pass the inside region 124 of the cup 20 adjacent the groove 64 and allow the ridge 90 to engage the groove 64 thereby relieving the compressive and expanding forces and allowing the components to assume the undeformed states. Removal of the insert 30 from the acetabular cup 20 by use of outward forces with substantial force components parallel to the generating axis (F—F of FIG. 2A) is extremely difficult since the engaging faces 125 and 126 on the liner and cup respectively are perpendicular to the generating axes and thus fail to produce any significant lateral forces compressing the insert or expanding the acetabular cup 20. Rather the forces will be essentially parallel to the generating axis and therefore due to the curved shape of the components will tend to expand the insert 30 and compress the cup 20 thereby locking the components together. Disassembly can be carried out only by use of instruments designed to be inserted into the slots 61—61 (FIG. 2) to apply lateral forces compressing the insert or expanding the cup. Due to the nature of the segmentation of these segemented open shell components described, relatively low lateral forces are needed to disassemble the components. Such lateral forces cannot be produced in these components in an implanted prosthesis. Even if such forces could be produced they would be resisted by the head of the femoral component 40 which prevents contraction of the insert 30 and by the acetabulum; and thus the liner 30 cannot be removed while it is in engagement with the femoral component 40. Hence dislocation resulting from distraction forces as the result of fluid between the femoral component and the liner cannot occur. Thus, for the case of a metal acetabular component which is very stiff compared to plastic and a plastic bearing insert dislocation of the hip is necessary to remove the plastic insert.

The increase in flexibility produced by the segmentation producing the segmented open shells described above can be understood by examining FIGS. 7A–D. FIGS. 7A and 7B illustrate a "segmented open shell" having increased wall flexibility in accordance with the present invention and FIGS. 7C and 7D illustrate an "open shell" both as described and defined above, and, FIGS. 7C and 7D also illustrate "open shells" of the prior art type disclosed in U.S. Pat. No. 4,123,806 to Amstutz et al. noted above. It may be seen from FIGS. 7B and 7A that the removal of the inferior shell segment removes a major lateral load supporting segment. Further also in shells where the wall thickness t is substantially smaller than the half the width or radius of the shell r (FIG. 7B) such segmentation eliminates most of the circumferential compressive stiffness of the wall thus making bending stiffness dominate. Since for such shells (e.g. segmented open shells) bending stiffness is much less than circumferential stiffness flexibility of the wall of the "segmented open shell" is greatly increased.

With regard to the screw 190, which may be utilized in the present invention, and referring to FIG. 4, it will be noted that in addition to the above-described screw structure the end of the screw 196 may be provided with radially disposed slots, as shown in FIG. 4A, which slots provide self-cutting action so that a cap need not be used in conjunction with the screw. Preferably, the screw is made of a metal alloy the same or similar to that of the metal acetabular cup 20 and it has been found to be preferable to provide several sized screws for different fixation conditions; the threads 198 are preferably large since they are for the purpose of screwing and holding into cancellous bone. Further, it has been found that the screw for fixation into the ischium 12, FIG. 1, is somewhat shorter than the screws used for fixation in the ilium 11 and pubis 13. Of course, the spherical underside 192 of the screw head 194 matches the spherical seats 69 of the apertures 66, 67, and 68 of FIG. 2.

It may be seen from FIG. 5 that the screw 190 can be moved through an angle $\beta$ about center 111 with the spherical underside 192 of screw 190 remaining in full contact with spherical seat 69 as observed by the motion of the screw axis from line 112 to 114 at which point the shank 199 contacts the edge 115 of hole 66 limiting further motion.

Before describing in detail the manner of assembly and disassembly of the metal acetabular cup 20 and the plastic bearing liner 30, and the assembly of the metal femoral cap 40 to the resected femur 16, a brief description of the surgical implantation or fixation technique is presented. The acetabulum, or acetabulum socket or cavity provided by the hip bone 10, FIG. 1, is reamed in an ordinary fashion as would be done for the implantation of any acetabular hip cup, such being well known to those skilled in the art, particularly orthopaedic surgeons skilled in the art. A trial component is then used to orient the acetabular cup to the acetabulum and is used to mark out the location of the holes to be drilled for accepting the screws 190. The metal acetabular cup 20 is provided with a slightly larger spherical outer surface 23 than the prepared acetabular cavity and the acetabular cup is then passed into place and the apertures 66, 67 and 68 are aligned with the prepared drill holes in the acetabulum. The screws 51, 52 and 53 of FIG. 1, which screws may be the screw 190 of FIG. 4, are then screwed into the hip bone providing the acetabular cavity to temporarily fixture the metal acetabular cup 20 to the hip bone. It will be understood that the spherical underside of the screw heads, e.g. spherical underside 192 of FIG. 4, engages the spherical seats 69 of the acetabular cup apertures and since the shank 199 of (FIG. 4) the screw is made to be much smaller than the diameter of the apertures, this allows the head of the screws to be pivoted about a point 111, FIG. 6, so that the screw may be oriented at an angle $\beta$ relative to the axis 112, FIG. 5, of the aperture. Thus, it will be understood, positioning variation is provided by the present invention and this positioning configuration has been found to be important in seeking out the best available bone for the screw to engage. Furthermore, this positioning variation is accomplished while maintaining excellent contact between the screw head and its spherical seats. The oblong spherical seats of the apertures, FIG. 2, allow for similar misalignment but also allow for a further change in the location of the screw within the confines of the seat thereby again enhancing effective utilization of existing bone stock and permitting a greater change in location of the screw within the aperture to permit the screw to engage the best available bone accessible through the aperture.

The plastic bearing liner 30 is now "snap-fitted" into place in the fixtured metal acetabular cup 20 in accordance with the teachings of the present invention. Spherically radially inwardly directed forces, such as may be generated digitally and quite easily by the fingers of the operating surgeon, are applied to the thinner wall regions 94—94 of the plastic bearing liner 30 to flex the lateral thinner wall portions inwardly to permit the interrupted annular ridge 90 of the plastic bearing liner 30 to be inserted into and engage the interrupted annular groove 64 of the metal acetabular cup 20 and the inwardly flexed bearing liner 30 in combination with the respective relieved inferior portions 38 and 89 of the acetabular cup 20 and plastic bearing liner 30, respectively, readily permit the flexed plastic bearing liner to be inserted, or "snap-fitted" into the metal acetabular cup 20. The key 65 of the acetabular cup 20 will be aligned with and received in the key-way 97 at the superior portion of the plastic bearing liner and the flat end portion of the wall 92 of the plastic bearing liner will be aligned with and engaged by the flat projection or ridge projecting inwardly at the inferior portion of the metal acetabular cup 20. The key and key-way, and engaged flat surfaces, resist relative rotation between the plastic bearing liner 30 and the metal acetabular cup 20 upon torsional stress being applied thereto during articulation of the hip joint. Further, it will be understood, as may be better seen in FIG. 5, the respective faces 60 and 85 of the acetabular cup 20 and plastic bearing liner 30 align, transversely, and present a common face for the assembled cup and liner and with the common relieved inferior portions thereof permitting a greater range of articulation of the femur bone without impingement with the liner and cup thereby further reducing the possibility of impingement of the cup and liner by the femur during joint articulation.

With the acetabular cup and plastic bearing liner now firmly in place in the acetabulum, the head of the femur 16 is resected or prepared by suitable instruments to provide a resected head, as shown in FIG. 6, complementary to the interior surface 44 of the metal femoral cup 40; more particularly, the resected head 19 of the femur 16 is prepared so as to provide the resected head with a flat portion 141 continuing into a spherical portion 142 continuing into a cylindrical portion 143. It will be understood that the outer dimensions of the resected femur head 19 are made somewhat larger than the inner dimensions of the inner surface 44 of the metal femoral cap 40 and the centrally drilled hole provided in the resected femur head 19 and femur neck 18 is made somewhat smaller in diameter than the diameter of the femoral cap stem 46 whereby the femoral cap may be press fitted onto the femur with such press fitting providing temporary fixation of the femoral cap to the femur. The hip joint is then reduced with the outer spherical surface 42 of the metal femoral cap 40 being received within the spherical inner surface 32 of the plastic bearing liner 30 for joint articulation. The articulation between the polished outer spherical surface 42 of the metal femoral head 40 and the spherical inner surface 32 of the plastic bearing liner 30 provide low friction, long wearing articulation and, the relatively larger articulation surfaces associated with the surface replacement prosthesis provide greater potential for extended wear resistance than do the smaller articulating surfaces associated with the conventional total hip prosthesis known to the prior art.

It will be further understood in accordance with the teachings of the present invention that the screws described above, providing temporary fixation of the metal acetabular cup to the hip bone providing the acetabulum provide temporary fixation during the period of time required for hip bone ingrowth and to the porous outer surface 23 of the acetabular cup which bone ingrowth provides the permanent fixation of the metal acetabular cup to the hip bone. Similarly, the press fit between the metal femoral cap 40 and the resected femur head 19 provides temporary fixation of the metal femoral cap to the femur during the time required for femur bone ingrowth at the resected head to grow into the porous inner surface 44 of the femoral cap to permanently fixture the femoral cap to the resected femur head. It has been found that such respective temporary fixations are sufficient to maintain the respective components fixtured during normal joint articulation and during the time required for bone ingrowth and biological permanent fixation.

In accordance with the further teachings of the present invention, the plastic bearing liner 30 may be readily and easily removed from the metal acetabular cup 20. Referring to FIG. 2, and as noted above, the lateral portions of the metal acetabular cup 20 are provided with generally opposed slots 66 into which a tool may be inserted and operated readily by digital force supplied by the operating surgeon to again flex the inner lateral regions of the plastic bearing liner walls 94—94 inwardly to flex the plastic bearing liner inwardly to permit the interrupted annular ridge 90 to be disengaged from the interrupted annular groove 64 and such engagement, in combination with the respective relieved inferior portions 28 and 89 of the cap and liner, permit the inwardly flexed plastic bearing liner 30 to be readily removed from the metal acetabular cup 20. It will be understood that in accordance with the further teachings of the present invention, the slots 61—61 could be provided on the outer surfaces of the plastic bearing liner 30, at the same positions, or mating opposed slots could be provided in both the metal acetabular cup and the plastic bearing liner.

Referring again to the recesses 101, 102 and 103, provided in the outer spherical surface 34 of the plastic bearing liner cup 30, FIG. 3, it will be understood that these recesses overlie the screw heads of the screws 51, 52 and 53 temporarily fixturing the metal acetabular cup to the hip bone and it will be understood that these recesses accommodate these screw heads even during any misalignment or relocation of the screws within the apertures as described above. Further, and in accordance with the teachings of the present invention, the plastic bearing liner portions providing the recesses engage the metal screw heads and prevent them from becoming unscrewed during joint articulation.

Referring again to FIG. 3B, it will be noted that the alternate plastic bearing liner shown herein, smaller than the plastic bearing liner of FIG. 3A, may be used in the event that the conventional metal femoral stem is used in the femur instead of the metal femoral cap 40 of the present invention, the spherical inner surface 132 of the plastic bearing liner alternate embodiment 130 of FIG. 3B being dimensioned to closely match the exterior surface of such metal femoral stem.

Still further in accordance with the teachings of the present invention, the bearing liner, instead of being plastic as described above, may be ceramic and in such alternate embodiment it will be understood that the relatively thin walls of the metal acetabular cup 20 will be flexed outwardly to permit the ceramic bearing liner to be inserted into and removed from the metal acetabular cup 20; it will be understood that the ceramic bearing liner is brittle and less flexible than the metal acetabular cup but will still undergo some slight inward flexing but due to the relieved inferior portions only a very slight outward flexing of the metal acetabular cup or very slight inward flexing of the ceramic liner, in combination with the relieved inferior portions, will readily permit the insertion and removal of a ceramic bearing liner from the metal acetabular cup.

An important advantage of a replaceable bearing liner is that a surface replacement type hip may be revised to a conventional total hip using a femoral stem without disturbing acetabular fixation by removing the plastic liner shown as embodiment 30 intended for use with a surface replacement femoral component and replacing it with the liner embodiment 130 intended for use with a femoral stem prosthesis.

Referring again to FIGS. 7A-D where it is shown that by open shell segmentation the flexibility of the side walls may be increased, it should be observed that this increase in flexibility will result in an increase in the amount of allowable engagement between the groove 64 (FIG. 2A) and the ridge 90 (FIG. 3A) for a given assembly load compared to a non-segmented open shell since the segmented open shell is more easily compressed. Thus, the strength of this engagement can be increased and/or manufacturing tolerances associated with this engagement can be less critical than those associated with a non-segmented open shell.

Referring now to FIGS. 8-10, there is illustrated a further alternate embodiment of the present invention also embodied as a multi-component hip joint prosthesis indicated by general numerical designation 218 and including a generally semi-hemispherical outer metal acetabular cup 220 and a generally semi-hemispherical inner plastic bearing liner 230. The cup and liner are illustrated in their assembled position in FIG. 8 and shown, respectively, in cross-section in FIGS. 9 and 10 with FIGS. 9 and 10 being similar to the cross-sectional views of FIGS. 2A and 3A, respectively, and it will be understood that the front views of the cup and liner 220 and 230 merely would be similar to the front views shown in FIGS. 2 and 3, respectively, and hence are not shown.

Acetabular cup 220 and plastic bearing liner 230 are structurally similar to the earlier described acetabular cup 20 and plastic bearing liner 30, that is the metal acetabular cup 220 and the plastic bearing liner 230 are each a "segmented open shell" as defined hereinabove with each having an inferior segment removed which increases the flexibility of the cup and liner wall thereby facilitating their assembly and disassembly by reducing the assembly and disassembly forces required. It will be recalled with regard to the "segmented open shell" of the present invention illustrated in FIGS. 7A and 7B and as taught in the associated specification hereinabove, that were a major load supporting inferior segment resisting assembly forces not removed, but present as shown in the case of the prior art "open shells" illustrated in FIGS. 7C and 7D, such inferior segment if present would resist the assembly (also disassembly) forces and would, as taught above, make the cup and liner more stiff in compression thereby requiring the application of greater assembly and disassembly forces to produce assembly and disassembly. In addition, as also taught above, this is particularly advantageous with regard to intraoperative assembly of the prosthesis within a surgical cavity.

Primarily, the hip joint prosthesis alternate embodiment 218 of the present invention differs from the earlier described embodiments due to the fact that the metal acetabular cup 220 and plastic bearing liner 230 are each provided with a protrusion, i.e. lateral protrusion, at their anterior and posterior wall portions, the posterior protrusions 221 and 231 of the cup 220 and liner 230, respectively, being shown in the cross-sectional drawings of FIGS. 9 and 10.

Referring now particularly to FIG. 9, the segmenting of the segmented open shell acetabular cup 220 will be described in detail. FIG. 9 is a cross-sectional view as noted above and is taken through the plane of symmetry which plane of symmetry, it will be understood, lies in the plane of the drawing. The metal acetabular cup 220 is segmented by a first cutting plane or planar cutting surface A'—A' perpendicular to the noted plane of symmetry; a second cutting plane or planar cutting surface C'—C' perpendicular to the plane of symmetry and intersecting the first planar cutting surface A'—A', the second planar cutting surface C'—C' removes a major load supporting inferior segment resisting assembly and disassembly forces same as in the embodiment of the present invention illustrated diagrammatically in FIGS. 7A and 7B and relieves the inferior portion 228 of the cup wall 222; a third cutting plane or planar cutting surface E—E perpendicular to the plane of symmetry and inclined at an angle $\theta$ with respect to the first cutting surface A'—A'; a first cylindrical cutting surface D'—D' perpendicular to the plane of symmetry and tangent to the second and third planar cutting surfaces C'—C' and E—E, respectively; and a second cylindrical cutting surface H—H perpendicular to the plane of symmetry and tangent to the first and third planar cutting surfaces A'—A' and E—E. The first planar cutting plane A'—A' is relieved or displaced medially from the center of curvature 225 as shown by the double headed arrow 227 extending between the cutting surface A'—A' and a parallel plane B'—B' extending through the center of curvature 225. It will be noted from FIG. 9 that such cutting surfaces define the cup face indicated by general numerical designation 260 and that the second through fifth cutting surfaces produce protrusions at the anterior (not shown) and posterior 221 portions of the wall 222 of the segmented open shell or metal acetabular cup 220.

The segmenting of such cutting surfaces may also be understood in the context of the closed shell 240 shown partially and in dashed outline in FIG. 9. The closed shell 240 is a solid of revolution (including the spherical wall 222 of the segmented open shell 220), has a generating axis F'—F' and has spherical inner and outer surfaces 241 and 242 (portions providing the spherical outer and inner surfaces 222 and 224, respectively, of cup 220). It will be noted and further understood that the above-described cutting surfaces, A'—A', etc., segment by passing or cutting through the wall and inner and outer spherical surfaces of the shell as is known by those skilled in the art in the segmenting of any shell.

Referring now to FIG. 10, it will be understood that the plastic bearing liner 230, as noted above, is also a segmented open shell being segmented by cutting surfaces A'—A', C'—C', E—E, D'—D' and H—H, as shown in FIG. 10, and which cutting surfaces are identical, or substantially identical, to the correspondingly identified cutting surfaces of FIG. 9. The cutting surfaces of FIG. 10 also define the face, indicated by general numerical designation 285, of the liner 230, and hence it will be understood that the faces 260 and 285 of the cup 220 and liner 230, respectively, are complementary as may be noted from the assembly view of FIG. 8. As may be understood by reference to FIGS. 9 and 10, generally, the superior portion of the respective faces 260 and 285 is defined by the planar cutting surface A'—A' and the inferior portion of the respective faces is defined by the remaining cutting surfaces. Further, cutting surfaces C'—C', D'—D', E—E and H—H also produce protrusions at the anterior (not shown) and posterior 231 portions of the wall 232 of the plastic bearing liner 230; the planar cutting surface C'—C' removes a major load supporting inferior segment resisting assembly and disassembly forces (same as in the embodiment of the present invention illustrated in FIGS. 7A and 7B) and relieves the inferior portion 289 of the liner wall 232 thereby increasing, particularly, the flexibility of the anterior and posterior wall portions which facilitates the insertion of the liner 230 into the cup 220 for assembly and the removal of the liner from the cup for disassembly. The liner 230 is provided with a spherical outer surface 233 for engaging the spherical inner surface 224 of the cup 220, and with a spherical inner surface 234 for articulating with the outer spherical surface of a spherical head such as the outer surface 42 of the femoral cap 40 of FIG. 1. The outer surface 233 and inner surface 234 may be either concentric or eccentric as shown in FIGS. 3A and 3B and described above.

As may be noted from FIG. 8, the posterior protrusions of the cup 220 and liner 230 of the alternate hip prosthesis embodiment 218 extend laterally beyond the corresponding portions of the cup 20 and liner 30 of the first embodiment indicated in dashed outline in FIG. 8. The significance and further advantages of these protrusions are illustrated in FIGS. 11-13.

Figure 11:
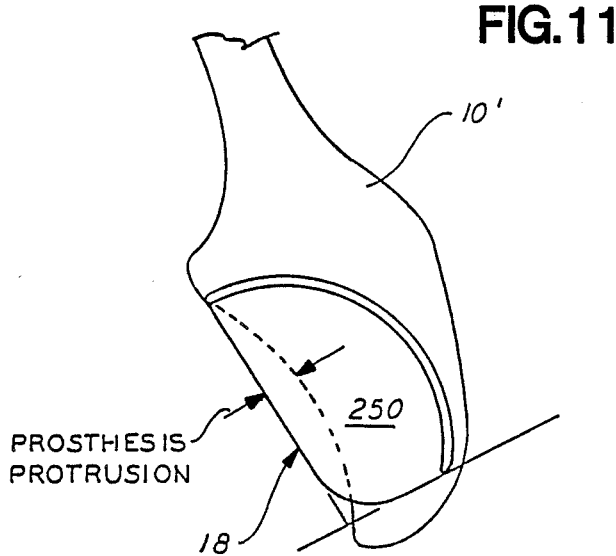
FIGS. 11-13 are diagrammatical illustrations showing the advantages of the further alternate embodiment and illustrating the features causing this embodiment to be the preferred embodiment.
Figure 12:
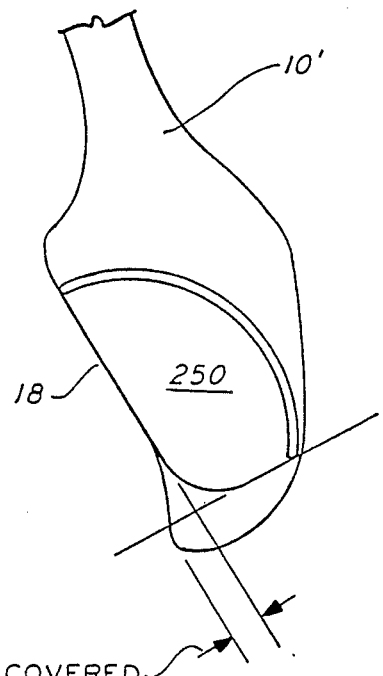
Figure 13:
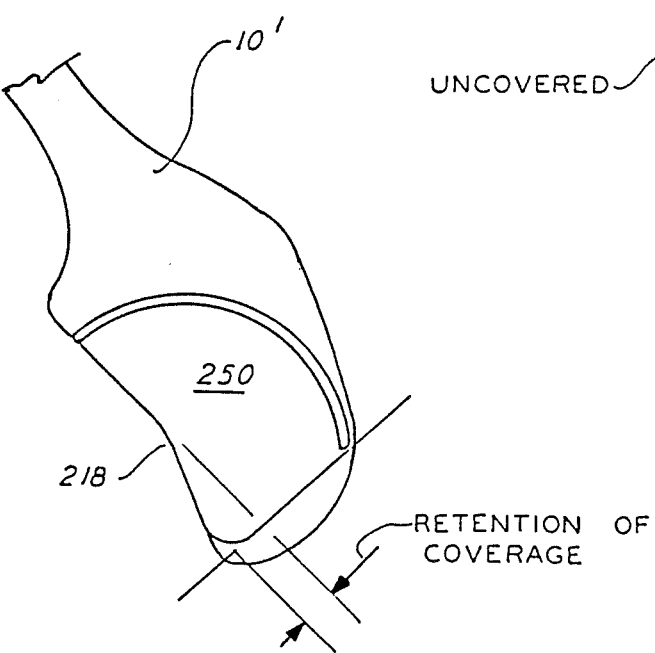

Referring now to FIGS. 11-13, the lateral portion of a natural hip bone 10' having a natural acetabulum or natural acetabular cavity 250 is illustrated in cross-section. Were the earlier described hip prosthesis embodiment 18 (FIG. 1) to be dimensioned so as to precisely fit or match the natural acetabular cavity 250, as illustrated in FIG. 11, a portion of the hip prosthesis 18 would protrude laterally beyond the borders of the natural acetabular cavity 250 as illustrated by the opposed arrows shown. Alternately, were the earlier described hip prosthesis 18 to be dimensioned so as not to protrude laterally beyond the border of the natural acetabular cavity 250, then as shown by the opposed arrows in FIG. 12, this would leave, undesirably, a substantial portion of the inferior aspect of the natural acetabular cavity 250 and its natural acetabular cartilage uncovered. However, as may be noted from FIG. 13, the alternate hip prosthesis embodiment 218 of the present invention eliminates the prosthesis extrusion illustrated in FIG. 11 and at the same time substantially covers the natural acetabular cavity 250 and its natural acetabular cartilage as shown. Accordingly, it will be understood that the alternate hip prosthesis embodiment 218 is the preferred embodiment of the present invention since it has better conformance to the shape of the natural acetabular cavity 250 and allows replacement of most of the surface of the natural acetabular cavity and acetabular cartilage without protrusion of the prosthesis beyond the bony borders of the natural acetabulum. Such protrusion (FIG. 11) is undesirable since such protrusion may produce impingement between the acetabular hip prosthesis and either natural bone or a femoral prosthesis component thereby producing undesirable shearing loads on the acetabular hip prosthesis causing loosening. Where, as in the alternate hip embodiment 218 illustrated in FIG. 13, the hip prosthesis 218 is kept entirely within the bony borders of the natural acetabulum, such impingement loading is avoided thereby reducing any tendency for loosening of the acetabular component due to such impingement.

It will be understood that the metal acetabular cup 220, similar to the earlier described metal acetabular cup 20, is also provided with a plurality of screw holes having recessed spherical seats for receiving metal screws (e.g. metal screw 90 of FIG. 4) to temporarily fixture the cup 220 to the hip bone (e.g. hip bone 10 of FIG. 1); two of such screw holes are shown in FIG. 9 and identified as 266 and 268. Also, similarly, the cup 220 and liner 230 are provided with mutually engageable retaining means for maintaining them together upon assembly, viz. respective mating annular groove 264 and annular ridge 290 of complementary configuration as shown in FIGS. 9 and 10, as with the annular groove 64 and annular ridge 90 of FIGS. 2A and 3A, the inferior aspect of the groove 264 and ridge 290 are interrupted or relieved inferiorly by the cutting planes C'—C' of FIGS. 9 and 10 which, in particular, increases the flexibility of the ridge 290 and permits the liner 230 to be readily "snap-fitted" into the cup 220 by the application of spherically inwardly directed assembly forces generated digitally and quite easily by the fingers of the operating orthopaedic surgeon.

Figure 14B:
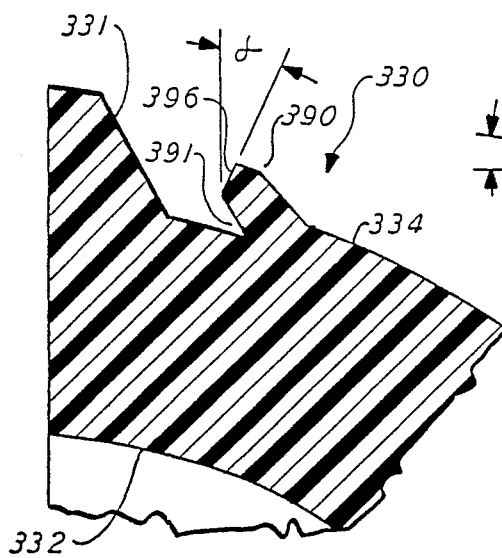
FIGS. 14A and 14B are, respectively, partial cross-sectional views of the superior aspect of the acetabular cup and plastic bearing liner of the alternate embodiment of FIGS. 8-10.

Referring now to FIGS. 14-19, there is shown a further alternate embodiment of the present invention including an alternate embodiment acetabular cup 320 (e.g. FIG. 14A) and an alternate plastic bearing liner 330 (e.g. FIG. 14B). For convenience of presentation, only the cross-sectional views of the upper face or rim portions of the cup 320 and liner 330 are shown because it will be understood that the cup 320 and liner 330 are each a "segmented open shell" as defined above with each having a major inferior load bearing segment resisting assembly and disassembly forces removed to increase the flexibility of the walls of the components and facilitate their assembly and disassembly. Except for the structural differences to be described, the cup 320 otherwise may be similar to either the cup 20 (FIG. 2A) or 220 (FIG. 9) and the liner 320 otherwise may be similar to the liner 30 (FIG. 3A), liner 130 (FIG. 3B) or liner 230 (FIG. 10).

Figure 14A:
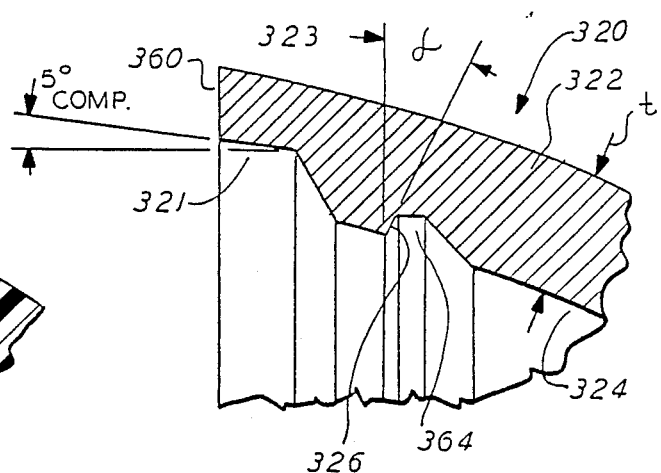
Figure 15B:
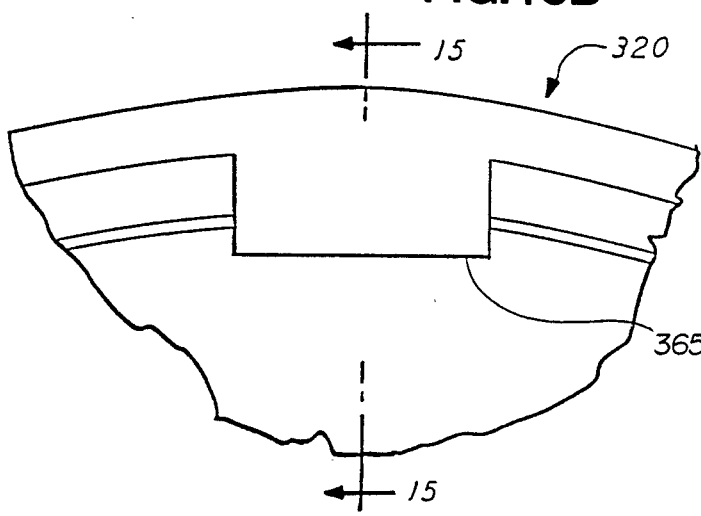
FIG. 15B is a front elevational view of the acetabular cup of the further alternate embodiment.
Figure 15A:
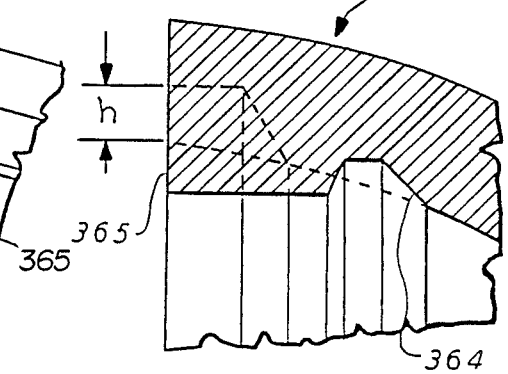
FIG. 15A is a cross-sectional view taken generally along the line 15—15 in FIG. 15B in the direction of the arrows.

As may be noted from FIG. 14A, the metal acetabular cup 320 in addition to the annular retaining groove 364 is provided with an annular recess 321 extending inwardly from the cup face 360, also, the face 326 of the retaining groove 364 is provided with a lead in angle which in the preferred embodiment is approximately 15°.

The thickness t, indicated by the opposed arrows in FIG. 14A, is determined primarily by considerations involving the thickness of the screw head (e.g. screw head 194 of FIG. 5) upon the screw head being fully recessed within its spherical seat (e.g. spherical seat 69 of FIG. 5). The use of the annular recess 321 increases the height of the key 365 (FIGS. 15A and 15B) by an amount h indicated by the double-headed arrow of FIG. 15A beyond the height of the key 65 of FIG. 2. This provides a larger key which is more effective in providing axial orientation of the plastic bearing liner, e.g. plastic bearing liner 334 of FIG. 14A, relative to the metal acetabular cup 320, in providing resistance against rotation of the plastic bearing member 334 in the metal cup 320 which upon assembly tends to roll with respect to the metal acetabular cup due to the engaging inner spherical surface 324 of the cup 320 and the outer spherical surface 334 of the plastic bearing liner 330, and in providing visual clues to the operating orthopaedic surgeon to assist in aligning the cup and liner for assembly particularly within a surgical cavity.

Figure 16B:
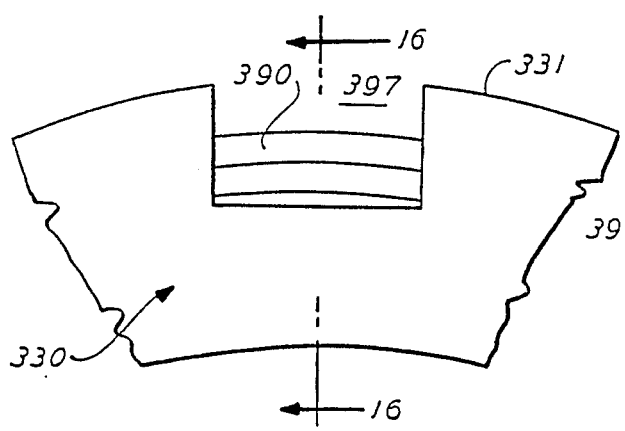
FIG. 16B is a partial front elevational view of the superior aspect of the plastic bearing liner of the further alternate embodiment of the present invention.
Figure 16A:
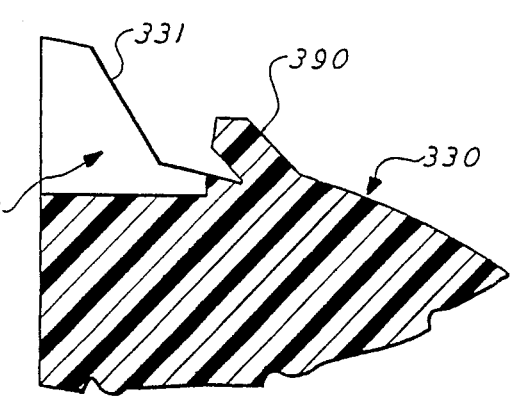
FIG. 16A is a cross-sectional view taken generally along the line 16—16 in FIG. 16B in the direction of the arrows.

The alternate embodiment plastic bearing liner 330, FIG. 14B, differs from the prior embodiments by being provided with an interrupted annular flange 331 which is complementary in shape to and which fits into the interrupted annular recess 321 (FIG. 14A) of the metal acetabular cup 320. In addition, the ridge or locking ridge 390 of FIG. 14B in this alternate embodiment differs from the prior embodiments ridge or locking ridges, e.g. ridge 90 (FIG. 3A) and ridge 290 (FIG. 10), by being provided with an undercut 391 for increasing the inward flexibility of the ridge 390 in bending. In addition, the face 396 of the locking ridge 390 is inclined at the angle to match the lead-in angle of the face 326 of the retaining groove 364 (FIG. 14A) formed in the metal acetabular cup 320. The plastic bearing liner 330 is provided with a keyway as shown in FIGS. 16A and 16B for receiving the key 365 (FIGS. 15A and 15B) in the same manner that the keyways receive the key in the alternate embodiments except that in this embodiment the key 365 and keyway are greater in height as mentioned above.

Figure 17:
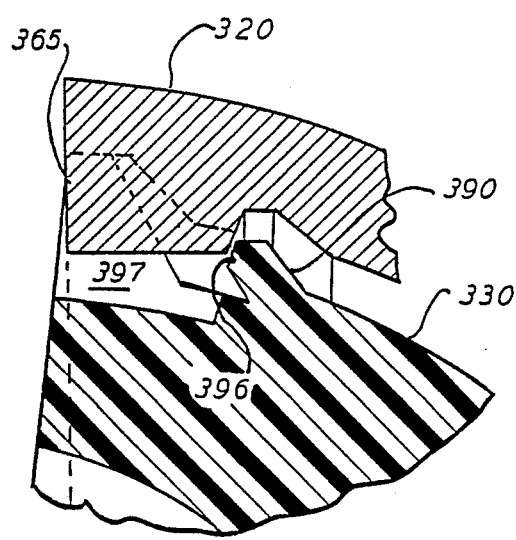
FIGS. 17-20 are sequential views showing respective stages in the assembly of the further alternate embodiment acetabular cup and plastic bearing liner.
Figure 18:
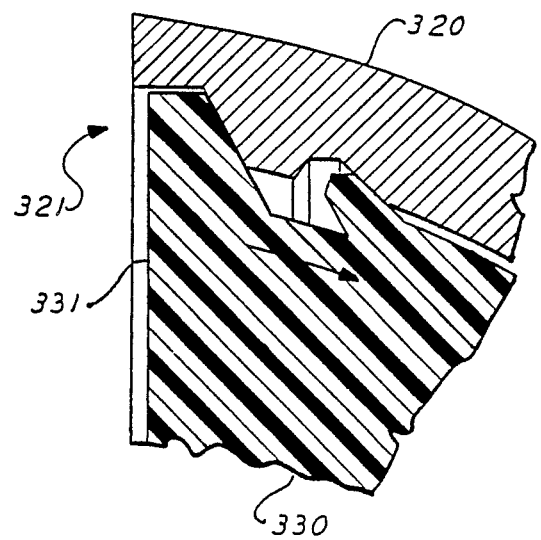
Figure 20:
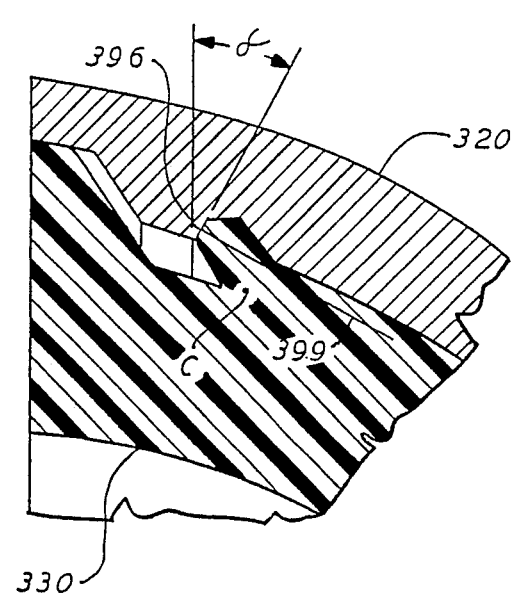

Upon assembly, FIG. 17, the superior aspect or portion of the plastic bearing liner 330 having the keyway 337 formed therein is first inserted into the metal acetabular cup 320 with the key 365 and keyway 397 aligned and with the face 396 of the locking ridge 390 engaging the back of the key 365; this partially traps the superior aspect or portion of the plastic bearing liner 330 in the metal cup 320. Now, either the anterior or posterior portion of the flange 331 of the plastic bearing liner 330 is inserted into the corresponding anterior or posterior portion of the recess 321 of the metal acetabular cup 320; this is illustrated in FIG. 18 which shows the posterior portion of the flange 331 engaging the posterior portion of the recess 321. Thus, at this point in the assembly, it will be understood that the flange 331 and recess 321 upon engagement help stabilize the plastic bearing liner 330 in the metal acetabular cup 320 against rotation in the direction of the arrows shown in FIG. 18 and prevents the above-noted rolling tendency of the spherical outer surface 334 of the liner 330 upon engaging the spherical inner surface 324 of the cup 320. At this point in the assembly, the opposite side of the plastic bearing liner insert 330, i.e. the anterior portion of the flange of the plastic bearing liner if the posterior portion is first engaged, or vice versa, is then "snap-fitted" into the recess 321 of the metal acetabular cup. This action produces deformation in the plastic bearing liner 320 which deformation takes two forms. First the anterior and posterior portions of the wall of the plastic bearing liner 330 flex inwardly due to their increased flexibility described above and secondly the locking ridge 390, which is interrupted or relieved inferiorly as described above to enhance its inward flexibility, also flexes inwardly thus facilitating assembly of the plastic bearing insert 330 with the metal acetabular cup 320; a fully assembled plastic bearing liner and metal acetabular cup are shown in FIG. 20.

Figure 19:
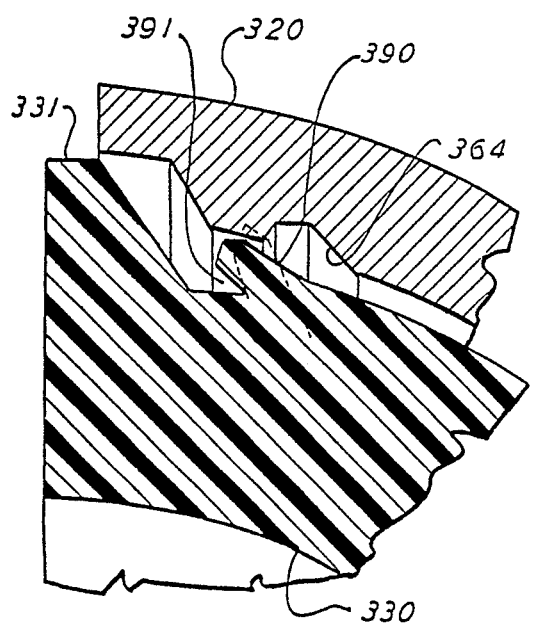

Referring to FIG. 19, the purpose of the lead-in angle $\alpha$ (FIGS. 14A and 14B) will now be more fully understood in that it will be understood that this angle $\alpha$ is needed to allow the flexible locking ridge 390 to move into the groove 364. Since the tip of the flexible locking ridge 390 first will flex or bend in the direction of the arrow of FIG. 18, the use of the matching lead-in angles $\alpha$ will facilitate the bending or snapping back of the flexible locking ridge 390 in the direction opposite to the direction of the arrow (FIG. 18) and into the groove 364. It will be understood that the lead-in angle $\alpha$ must not be so great that the approximate location of the flexure center C (FIG. 20) of the flexible locking ridge 390 lies above a line 399 drawn perpendicular to the face 396 of the locking ridge 390.

It will be understood by those skilled in the art, i.e. the joint prosthesis art, that the terms of reference used in the appended claims and hereinabove, viz. anterior and posterior, inferior and superior, medial and lateral, and the orientation of the acetabular components and bearing liners as shown in the drawings, except for FIG. 1, are with reference to the left natural acetabulum as viewed facing the human body, and that such terms are merely terms of reference.

Further, it will be understood by those skilled in the art that the prosthesis described above is the subject of many variations and modifications all within the scope of the present invention and that the present invention is limited only by the scope of the appended claims.

What is claimed is:

1. A joint prosthesis comprising first and second cup-shaped components for being assembled together, the assembly of said components requiring the application thereto of assembly forces, said first component being a segmented open shell including a wall defining part spherical inner and outer surfaces, said segmented open shell has a face and a plane of symmetry; wherein the face of said segmented open shell is defined by: (i) a first planar surface substantially perpendicular to said plane of symmetry, (ii) a second planar surface substantially perpendicular to said plane of symmetry and angularly aligned to said first planar surface, and (iii) a first pair of curved surfaces on opposite sides of said plane of symmetry and defining portion of a cylinder aligned perpendicular to said plane of symmetry and tangent to said first and second planar surfaces; wherein the alignment of said surfaces relative to one another increases the flexibility of the wall and facilitates assembly of said components.

2. A joint prosthesis according to claim 1 wherein said second component comprises a segmented open shell having a face, a wall defining part spherical inner and outer surfaces and a plane of symmetry the face of the second component defining surfaces substantially aligned with the surfaces defining the face of said first component for increasing the flexibility of the second component wall which facilitates assembly of said components.

3. A joint prosthesis comprising first and second cup-shaped components for being assembled together, the assembly of said components requiring the application thereto of assembly forces, said first component being a segmented open shell including a wall defining part spherical inner and outer surfaces, said segmented open shell has a face and a plane of symmetry, the face of said segmented open shell is defined by (i) a first planar surface substantially perpendicular to said plane of symmetry, (ii) a second planar surface substantially perpendicular to said plane of symmetry and angularly aligned to said first planar surface, (iii) a pair of third planar surfaces disposed on opposite sides of the plane of symmetry and defining a plane substantially perpendicular to said plane of symmetry and inclined at an angle with respect to said first planar surface, (iv) a pair of first curved surfaces disposed on opposite sides of the plane of symmetry and defining a portion of a cylinder aligned substantially perpendicular to said plane of symmetry and tangent to said second and third planar surfaces and (v) a pair of second curved surfaces disposed on opposite sides of the plane of symmetry and defining a portion of a second cylinder aligned substantially perpendicular to said plane of symmetry and tangent to aid first and third planar surfaces; wherein the alignment of said surfaces relative to one another increases the flexibility of the wall and facilitates assembly of said components; and said segmented open shell having anterior and posterior portions and wherein said second through fifth surfaces produce protrusions at the anterior and posterior inferior portions of said segmented open shell.

4. A joint prosthesis according to claim 3 wherein said second component comprises a segmented open shell having a face, a wall defining a part of sphere and a plane of symmetry the face of the second component defining surfaces substantially aligned with the surfaces defining the face of said first component for increasing the flexibility of the second component wall which facilitates assembly of said components.

5. A joint prosthesis according to claim 1 or 3 wherein said second planar surface is substantially perpendicular to said first planar surface.

6. A joint prosthesis according to claim 1, 2, 3 or 4 wherein said components are provided with mutually engageable retaining means for maintaining said components together upon assembly and wherein said segmenting increases the flexibility of the retaining means and facilitates the engagement of said retaining means during assembly of said components.

7. A joint prosthesis according to claim 6 wherein said retaining means comprise a groove and a ridge one of which is provided on said first component and the other of which is provided on said second component, said groove and ridge having inferior portions intersecting at least one of said surfaces such that said ridge defines a segment of an annular ridge which increases its flexibility and facilitates engagement with said groove.

8. A joint prosthesis according to claim 7 wherein said components are provided with mutually engageable flange and recess for stabilizing said components during assembly by preventing relative rotation therebetween during assembly.

9. A joint prosthesis according to claim 1, 2, 3 or 4 wherein said first component has segmented outer and inner surfaces of revolution defining said wall and which surfaces are eccentric to each other causing said wall to be thinner in lateral regions which increases the flexibility of said regions which facilitates assembly of the components.

10. A joint prosthesis according to claim 9 wherein said eccentricity produces thickening of the wall in a superior region which is highly loaded during use of the prosthesis thereby increasing load resistance of the component.

11. A joint prosthesis according to claim 1, 2, 3 or 4 wherein said joint prosthesis is a hip joint prosthesis, wherein said first component is a plastic bearing liner and said second component is a metal acetabular cup for being secured to a hip bone, wherein the respective second planar surfaces of said liner and cup each define an inferior portion of said prosthesis, and wherein said plastic bearing liner is for being inserted into said metal acetabular cup for said assembly.

12. A joint prosthesis according to claim 7 wherein said ridge and said groove each are disposed in a plane aligned generally parallel to the first planar surfaces, and are provided with a face inclined at a predetermined angle away from the first planar surfaces of said respective components and said inclined faces enhancing the engagement of said ridge with said groove.

13. A hip joint prosthesis, comprising:
 a generally semi-hemispherical acetabular cup and a generally semi-hemispherical bearing liner each having a face, anterior, posterior and inferior wall portions and said bearing liner for being inserted into and removed from said acetabular cup, said acetabular cup and said bearing liner each being a segmented open shell aligned for increasing the flexibility of aid anterior and posterior wall portions which facilitates insertion and removal of said bearing liner into and out of said acetabular cup, said acetabular cup and said bearing liner each have a plane of symmetry and each said face having superior and inferior portions, said superior face portion of said cup and said liner each being defined by a first planar surface substantially perpendicular to said plane of symmetry, and said inferior face portion of said cup and liner each being defined by: (i) a second planar surface substantially perpendicular to said plane of symmetry and to said first planar surface and (ii) a first pair of curved surfaces on opposite sides of said plane of symmetry and defining a portion of a cylinder aligned substantially perpendicular to said plane of symmetry and tangent to said first and second planar surfaces.

14. A hip joint prosthesis comprising a generally semi-hemispherical acetabular cup and a generally semi-hemispherical bearing liner each having a face, anterior, posterior and inferior wall portions and said bearing liner for being inserted into and removed from said acetabular cup, said acetabular cup and said bearing liner each being a segmented open shell aligned for increasing the flexibility of said anterior and posterior wall portions which facilitates insertion and removal of said bearing liner into and out of said acetabular cup, wherein said acetabular cup and said plastic bearing liner each have a plane of symmetry and each said face having superior and inferior portions, said superior face portion of said cup and said liner each being defined by a first planar surface substantially perpendicular to said plane of symmetry and said inferior face portion of said cup and said liner each being defined by: (i) a second planar surface substantially perpendicular both to said plane of symmetry and to said first planar surface, (ii) a pair of third planar surfaces disposed on opposite sides of said plane of symmetry and defining a plane substantially perpendicular to said plane of symmetry and inclined at an angle with respect to said first planar surface, (iii) a pair of first curved surfaces disposed on opposite sides of the plane of symmetry and defining portions of a cylinder aligned substantially perpendicular to said plane of symmetry and tangent to said second and third planar surfaces, and (iv) a pair of second curved surfaces disposed on opposite sides of said plane of symmetry and defining portions of a second cylinder aligned substantially perpendicular to said plane of symmetry and tangent to said first and third planar surfaces; and said cup and liner each have anterior and posterior portions and wherein said second and third planar surfaces and said first and second curved surfaces produce protrusions at said anterior and inferior portions.

15. A hip joint prosthesis according to claim 13 wherein upon said bearing liner being inserted into said acetabular cup said cup and liner having generally a common center of curvature and wherein aid superior face portion is relieved a predetermined distance medially from a plane passing through said center of curvature and parallel to said first planar surface.

16. A joint prosthesis according to claim 15 wherein said acetabular cup and said bearing liner are provided with mutually engageable retaining means for maintaining said cup and liner together upon assembly and wherein said segmenting increases the flexibility of the retaining means and facilitates the engagement of said retaining means during assembly of said cup and liner.

17. A joint prosthesis according to claim 13, or 14 wherein said acetabular cup and said bearing liner are provided with mutually engageable retaining means for maintaining said cup and liner together upon assembly and wherein said segmenting increases the flexibility of the retaining means and facilitates the engagement of said retaining means during assembly of said cup and liner.

18. A hip joint prosthesis according to claim 17 wherein said retaining means comprise an annular groove and an annular ridge one of which is provided on said acetabular cup and the other of which is provided on said bearing liner, said groove and ridge having inferior portions intersecting at least one of said surfaces such that said ridge defines a segment of an annular ridge which increases its flexibility and facilitates engagement with said groove.

19. A joint prosthesis according to claim 18 wherein said ridge is provided on said acetabular cup and said groove is provided on said bearing liner.

20. A hip joint prosthesis according to claim 13 or 14 wherein said acetabular cup is provided with an annular recess adjacent said cup face and said bearing liner provided with a flange adjacent said liner face, said recess and flange having inferior portions interrupted by one or more of said surfaces and having anterior and posterior portions, one of aid anterior and posterior portions of said recess and flange engageable upon insertion of said liner into aid cup to prevent relative rotation therebetween and thereby stabilize said cup and liner during said insertion.

21. A hip joint prosthesis component, comprising:
a generally semi-hemispherical acetabular cup having anterior, posterior and inferior wall portions, said acetabular cup being a segmented open shell for increasing the flexibility of said anterior and posterior wall portions wherein said acetabular cup has a plane of symmetry and a face having superior and inferior portions, said superior face portion defined by a first planar surface substantially perpendicular to said pane of symmetry, and said inferior face portion defined by: (i) a second planar surface substantially perpendicular to said plane of symmetry and aligned at an angle to said first planar cutting surface and generally forming a right angle therewith, and (i) a pair of first curved surfaces on opposite sides of said plane of symmetry and defining a portion of a cylinder aligned substantially perpendicular to said plane of symmetry and tangent to said first and second planar surfaces.

22. A hip joint prosthesis component comprising a generally semi-hemispherical acetabular cup having anterior, posterior and inferior wall portions, said acetabular cup being a segmented open shell for increasing the flexibility of said anterior and posterior wall portions wherein said acetabular cup has a plane of symmetry and a face having superior and inferior portions, said superior face portion defined by a first planar surface substantially perpendicular to said plane of symmetry and said inferior face portion defined by: (i) a second planar surface substantially perpendicular to said plane of symmetry and aligned at an angle to said first planar surface and generally forming a right angle therewith, (ii) a pair of third planar surfaces on opposite sides of said plane of symmetry and defining a plane substantially perpendicular to said plane of symmetry and inclined at an angle with respect to said first planar surface, (iii) a pair of first curved surfaces on opposite sides of said plane of symmetry and defining portions of a cylinder aligned substantially perpendicular to said plane of symmetry and tangent to said second and third planar surfaces, and (iv) a pair of second curved surfaces on opposite sides of said plane of symmetry and defining portions of a cylinder aligned substantially perpendicular to said plane of symmetry and tangent to said first and third planar surfaces; and said acetabular cup having anterior and posterior portions and wherein said second and third planar surfaces and said first and second cylindrical surfaces produce protrusions at said anterior and posterior portions.

23. A hip joint prosthesis component, comprising:
a generally semi-hemispherical bearing liner having anterior, posterior and inferior wall portions, said bearing liner being a segmented open shell for increasing the flexibility of said anterior and posterior wall portions wherein said bearing liner has a plane of symmetry and a face having superior and inferior portions, said superior face portion defined by a first planar surface substantially perpendicular to said plane of symmetry, and said inferior face portion defined by: (i) a second planar surface substantially perpendicular to said plane of symmetry and to said first planar surface and (ii) a pair of first curved surfaces disposed on opposite sides of said plane of symmetry and defining portions of a cylinder aligned substantially perpendicular to said plane of symmetry and tangent to aid first and second planar cutting surfaces.

24. A hip joint prosthesis component comprising a generally semi-hemispherical bearing liner having anterior, posterior and inferior wall portions, said bearing liner being a segmented open shell for increasing the flexibility of said anterior and posterior wall portions wherein said bearing liner has a plane of symmetry and a face having superior and inferior portions, said superior face portion defined by a first planar surface substantially perpendicular to said plane of symmetry and said inferior face portion defined by: (i) a second planar surface substantially perpendicular both to said plane of symmetry and to said first planar surface, (ii) a pair of third planar surfaces on opposite sides of the plane of symmetry and defining a plane substantially perpendicular to said plane of symmetry and inclined at an obtuse angle with respect to said first planar surface, (iii) a pair of first curved surfaces on opposite sides of said plane of symmetry and defining portions of a cylinder aligned substantially perpendicular to said plane of symmetry and tangent to said second and third planar surfaces, and (iv) a pair of second curved surfaces on opposite sides of said plane of symmetry and defining portions of a cylinder aligned substantially perpendicular to said plane of symmetry and tangent to said first and third planar surfaces; and said plastic bearing liner having anterior and posterior portions and wherein said second and third planar surfaces and said first and second curved surfaces produce protrusions at said anterior and posterior portions.

25. A joint prosthesis according to claim 7 wherein said ridge is provided with an undercut to enhance its inward flexibility and further facilitate its engagement with said groove.

* * * * *